United States Patent [19]

Canavesi et al.

[11] 4,301,308

[45] Nov. 17, 1981

[54] PROCESS FOR THE PREPARATION OF O-CRESOL AND 2,6-XYLENOL

[75] Inventors: Roberto Canavesi, Bollate; Ferdinando Ligorati, Usmate; Giancarlo Aglietti, Milan, all of Italy

[73] Assignee: Societe Italiana Resine S.I.R. S.p.A., Turin, Italy

[21] Appl. No.: 927,134

[22] Filed: Jul. 21, 1978

Related U.S. Application Data

[63] Continuation of Ser. No. 772,722, Feb. 28, 1977, which is a continuation of Ser. No. 633,702, Nov. 20, 1975, abandoned.

[51] Int. Cl.$^3$ .................. C07C 37/01; C07C 37/16
[52] U.S. Cl. ...................................... 568/804
[58] Field of Search ............................ 568/804

[56] References Cited

U.S. PATENT DOCUMENTS 3,367,981  2/1968  Napolitano ................. 568/804
3,426,358  2/1968  Schlichting ................. 568/804
3,624,163  11/1971  Del Bel ..................... 260/621 R
3,737,466  6/1973  Sharp et al. ................ 568/804

FOREIGN PATENT DOCUMENTS 600837  4/1948  United Kingdom ........... 260/621 R
600839  4/1948  United Kingdom ........... 568/804
602257  5/1948  United Kingdom ........... 260/620 R

*Primary Examiner*—Werren B. Lone
*Attorney, Agent, or Firm*—Christie, Parker & Hale

[57] ABSTRACT

0-cresol and 2,6-xylenol are prepared by flowing a gaseous stream of methanol and phenol in a molar ratio of phenol to methanol of from 1:1 to 1:9 through a fluidized bed of alumina particles at a temperature of from 200° to 400° C., said alumina being in the eta, gamma or chi crystallographic form, having a surface area of from 100 to 500 m$^2$/g and an overall pore volume of from 0.3 to 0.6 ml/g and having been pre-treated with a stream of air or inert gas at a temperature of the order of 500° C. for at least 2 hours.

7 Claims, No Drawings

PROCESS FOR THE PREPARATION OF O-CRESOL AND 2,6-XYLENOL

CROSS REFERENCE TO RELATED APPLICATIONS

This is a continuation of application Ser. No. 772,722, filed Feb. 28, 1977 which is a continuation of application Ser. No. 633,702, filed Nov. 20, 1975, now abandoned.

The present invention relates to improvements in the alkylation process of phenol with methanol, with particular reference to the preparation of o-cresol and 2,6-xylenol by contacting a gaseous stream containing phenol and methanol with alumina particles in the form of a fluidized bed.

The methylated derivatives of phenol are technically useful inasmuch as they are employed in the preparation of resins, plasticizers, antioxidants, disinfectants and agricultural chemical products.

More recently 2,6-xylenol has found applications in the synthesis of valuable polymeric products such as polyphenylene oxide.

The methylated derivatives of phenol can be obtained as by-products in the production of coke and the refining treatment of petroleum, or they can be synthetized by alkylation of phenol with methanol in either the gaseous or the liquid phase.

In the liquid phase processes, the alkylation is carried out at a temperature of 200°–400° C., under a pressure of 10–70 atm. using a zinc halide as catalyst, as in U.S. Pat. Nos. 2,601,621, 3,439,048 and 3,707,038; British Pat. Nos. 1,125,077 and 1,112,138; French Pat. No. 1,478,038 and German Pat. No. 1,281,448.

Other catalysts useful for the purpose are aluminum methylate or phenate described in British Pat. Nos. 1,102,309 and 1,060,036 and German Pat. No. 1,265,755.

In the gaseous phase processes, a gaseous stream containing phenol and methanol is contacted with a granular metallic oxide catalyst in the form of a fixed-bed, operating at a temperature of about 175°–500° C.

In particular, the conditions can be controlled so as to produce mainly anisole (British Pat. No. 600,837), o-cresol and 2,6-xylenol (British Pat. Nos. 600,837, 600,839 and 602,257 and J. Chem. Soc. 1145, 84), or more highly methylated products up to a hexamethylbenzene (British Pat. No. 600,898). The liquid phase processes present essentially the disadvantages related to the low selectivity for the required reaction products.

In the gaseous phase processes it is difficult to control the reaction progress, in particular because the reaction is highly exothermic.

Therefore there is an abundant formation of by-products and moreover, the catalyst rapidly loses its activity, so that frequent regeneration is required; this making the process difficult to apply on an industrial scale.

In any case the separation of the desired products of the reaction from the by-products is burdensome, particularly when a high degree of purity is required, for example, in the case of the 2,6-xylenol capable of yielding polyphenylene oxide. It has now been discovered that it is possible to prepare o-cresol and 2,6-xylenol, without the disadvantages of the prior art, or at least with a substantial reduction of such disadvantages.

According to the present invention, o-cresol and 2,6-xylenol are prepared by a process which consists essentially in flowing a gaseous stream containing methanol and phenol in a molar ratio of said phenol to said methanol from 1:1 to 1:2, through a fluidized bed of alumina particles from 20 to 100 microns in size, operating at a temperature of from 200° to 400° C. and with an alumina in the eta ($\eta$), gamma ($\gamma$) or chi ($\chi$) crystallographic form, having a surface area of from 100 to 500 m$^2$/g and an overall pore volume of from 0.3 to 0.6 ml/g, said alumina having been pre-treated with a stream of air or inert gas at a temperature of from 450° to 550° C. for a period of at least 2 hours.

It is preferable to use eta ($\eta$) alumina with an overall pore volume of from 0.3 to 0.5 ml/g and a surface area of from 250 to 400 m$^2$/g, in which at least 90% of the said volume is attributable to pores with a radius of less than 40 Å and at least 90% of the said area is attributable to pores with a radius of less than 30 Å. The best results are obtained with eta ($\eta$) alumina having an overall pore volume of the order of 0.4 ml/g, at least 90% of the said volume being attributable to pores with a radius of less than 30 Å and a surface area of the order of 350 m$^2$/g, at least 90% of the said area being attributable to pores with a radius of less than 20 Å.

It is known that eta ($\eta$) alumina, which can, for example, be obtained by heating bayerite ($\beta$.Al$_2$O$_3$.3H$_2$O) in air at temperatures of 250° to 500° C., crystallizes in the cubic system (spinel).

The other stated characteristics of the alumina can be determined according to the known B.E.T. method, by absorption of nitrogen, at the temperatures of liquid nitrogen ($-195$° C.).

According to the process of the present invention o-cresol and 2,6-xylenol are prepared by operating with a fluidized catalyst.

This purpose is usefully served by microspheroidal or granular alumina, preferably with an average diameter of 50 microns, containing no granules with a diameter of more than 100 microns or less than 20 microns.

The fluidization of this alumina can be achieved with a minimum linear velocity of the gaseous stream of the order of 0.2 cm/sec. a value easily achievable in industrial reactors.

In the process of the invention, it is also possible, though not convenient, to dilute the gaseous stream with inert gases, such as, for example, nitrogen. Thus, according to a preferred embodiment of the process of the invention, the gaseous stream consists of phenol and methanol.

Moreover, the reaction temperature is kept at a value of from 200° to 400° C. and preferably from 250° to 300° C., selecting the higher temperatures when it is intended to obtain a prevalent formation of products with a higher degree of methylation.

As aforementioned, the minimum linear velocity of the gaseous stream for the fluidization of catalyst is generally of 0.2 c/sec. and said velocity generally ranges from 0.2 to 40 cm/sec.

The residence time under the reaction conditions can range from 1 to 35 seconds.

It should be noted that the linear velocity and residence time refer to an empty reactor (free of catalyst) and to the temperature and pressure conditions of the reaction, the pressure being usually atmospheric, although it is also possible to operate at a pressure higher or lower than atmospheric.

According to the process of the present invention, the alumina is subjected to a preliminary heat treatment before use.

For this purpose a stream of air or inert gas, such as nitrogen, for instance, is made to flow through the alumina particles, while maintaining a temperature of the order of 500° C. (b 450°–550° C.). Preferably, the operation is effected with the alumina fluidized.

The pre-treatment of the alumina is important in view of the characteristics displayed by the latter in the methylation reaction of the phenol.

The pre-treatment time generally ranges from 2 to 6 hours. Times of less than 2 hours are insufficient for the purposes of the invention, whilst times exceeding 6 hours are usually not necessary.

When operating according to the process of the present invention it is possible to produce o-cresol and 2,6-xylenol from methanol and phenol under perfectly controlled conditions and with high activity and selectivity values.

Consequently, there are obtained the advantages relating to the obtaining of desired reaction products requiring slight treatments for their separation and purification.

In particular, the desired reaction products can be recovered from the gaseous stream issuing from the reactor, by means of cooling followed by conventional treatments of extraction with solvents, of distillation and of crystallization.

A fundamental advantage of the process of the present invention consists in the long life of the catalyst under the operation conditions without need for regeneration.

The choice of the type of alumina used is fundamental for the process described, particularly the crystallographic form of the said alumina and the characteristics of the volume of the pores and the surface area, as well as the distribution of the said pores. The best results are obtained with eta ($\eta$) alumina, whilst inferior results are obtained when using gamma ($\gamma$) or chi ($\chi$) alumina.

Other types of alumina, such as alpha ($\alpha$) or gamma and alpha ($\gamma + \alpha$) alumina do not show any appreciable activity in the methylation process of phenol.

EXAMPLE 1

Use is made of a glass reactor, of tubular shape, with an internal diameter of 25 mm, provided with an outer gap for heat exchange and a porous baffle at the bottom. The reactor is charged with 160 grams of alumina in granules of 20 to 100 microns of the following characteristics:

crystallographic form: eta ($\eta$);
overall volume of the pores: 0.4 ml/g; (25% of the said volume is due to pores with a radius of less than 12 Å and 90% to pores with a radius of less than 30 Å.
surface area: 360 m$^2$/g (25% of the said area is due to pores with a radius of less than 11 Å and 90% to pores with a radius of less than 21 Å);
Bulk density: 1.25 g/ml;
Average diameter of the granules: 50 microns.

Air is introduced at the bottom of the reactor and made to flow within the reactor at a velocity of 5 cm/sec. while the temperature is raised to about 500° C.

This temperature and these fluidization conditions are maintained for 4 hours.

Nitrogen is then substituted for air, whilst the temperature is lowered to 250° C. and the stream of nitrogen is gradually replaced by a gaseous stream of phenol and methanol in a molar ratio of 1:1.

In particular, one feeds in 0.35 volumes of the methanol and phenol mixture (considered as liquids) per hour and per volume of fluidized catalyst.

The reaction temperature is 250° C. and the residence time is 7 seconds.

The reaction products, recovered at the top of the reactor, are subjected to analysis and it is established that there is a 50% molar conversion with respect to the phenol feed, with a selectivity of 40% in moles for the anisole, 40% in moles for the o-cresol and 20% in moles for the 2,6-xylenol.

Other conditions being left unchanged, the temperature is increased to 300° C. and one obtains a 60% conversion of the phenol, and the following selectivity values: anisole 3%, o-cresol 50%, 2,6-xylenol 47%.

EXAMPLE 2

The procedure is similar to that of Example 1. The reactor containing the pre-treated alumina is fed with phenol and methanol in a molar ratio of 1:2.

Operating at 250° C., the phenol is converted to the extent of 55%, with the following selectivity values: anisole 47%, o-cresol 30%, 2,6-xylenol 15%.

Operating at 300° C., the phenol is converted to the extent of 70%, with the following selectivity values: anisole 5%, o-cresol 30%, 2,6-xylenol 45%.

EXAMPLE 3

The procedure is as in Example 1, using granular alumina having a gamma ($\gamma$) crystallographic form, an overall pore volume of 0.4 ml/g and a surface area of 180 m$^2$/g. By reacting phenol and methanol in conditions similar to those of Example 1, the following results are obtained:

at 250° C. the phenol is converted to the extent of 20%, with the following selectivity values: anisole 40%, o-cresol 40%, 2,6-xylenol 10%.
At 300° C. the phenol is converted to the extent of 30%, with the following selectivity values: anisole 50%, o-cresol 30%, 2,6-xylenol 20%.

EXAMPLE 4 (comparison)

One operates according to the procedure of Example 3, using alumina of gamma and alpha ($\gamma + \alpha$) crystallographic form, with a surface area of 40 m$^2$/g. There is practically no interaction between the phenol and the methanol.

EXAMPLE 5

The reactor of Example 1 is used, into which one charges 160 grams of granular alumina, of eta ($\eta$) crystallographic form, with a surface area of 350 m$^2$/g and an overall pore volume of 0.38 ml/g, the other characteristics of said alumina being similar to those of the alumina of Example 1. Activation is effected by means of a stream of air in the conditions of Example 1 and subsequently the reactor is fed with a gaseous stream of phenol and methanol (molar ratio 1:1) at a rate of 0.35 volumes (as liquid) per volume of fluidized catalyst and per hour.

Moreover, the operation is carried out at 210° C. and with a residence time of 5 seconds.

In these conditions the phenol is converted to the extent of 40% with a selectivity of 70% for the anisole and 30% for the o-cresol.

EXAMPLE 6

The procedure is as in Example 5, feeding the reactor with phenol and methanol in a molar ratio of 1:2 and keeping the temperature at 250° C.

With the other conditions similar to those of Example 5 the phenol is converted to the extent of 60% and the selectivity is equal to 50% for the anisole and 40% for the o-cresol.

What we claim is:

1. A method for preparing o-cresol and 2,6-xylenol, which comprises flowing a gaseous stream containing methanol and phenol in a molar ratio of said phenol to said methanol from 1:1 to 1:2, through a fluidized bed of alumina particles from 20 to 100 microns in size, operating at a temperature of from 200° C. to 400° C. the alumina being in the eta ($\eta$) crystallographic form, having a surface area of from 100 to 500 m$^2$/g and an overall pore volume of from 0.3 to 0.6 ml/g, said alumina having been pre-treated with a stream of air or inert gas at a temperature of from 450° to 550° C. for a period of at least 2 hours.

2. The method of claim 1, wherein the eta ($\eta$) alumina has an overall pore volume of from 0.3 to 0.5 ml/g and a surface area of from 250 to 400 m$^2$/g, at least 90% of said volume being attributable to pores with a radius of less than 40 Å and at least 90% of said area being attributable to pores with a radius of less than 30 Å.

3. The method of claim 1, wherein the eta ($\eta$) alumina has an overall pore volume of the order of 0.4 ml/g and a surface area of the order of 350 m$^2$/g, at least 90% of said volume being attributable to pores with a radius of less than 30 Å and at least 90% of said surface area being attributable to pores with a radius of less than 20 Å.

4. The method of claim 1, wherein said particles have an average diameter of 50 microns.

5. The method of claim 1, wherein said alumina is pre-treated for a period of from 2 to 6 hours.

6. The method of claim 1, wherein said fluidized bed is at a temperature of from 250° to 300° C.

7. The method of claim 1, wherein the linear velocity of said gaseous stream is from 0.2 to 40 cm/second and the residence time of said gaseous stream is from 1 to 15 seconds.

* * * * *